US008114665B2

(12) United States Patent
Wu et al.

(10) Patent No.: US 8,114,665 B2
(45) Date of Patent: Feb. 14, 2012

(54) PROMOTERS AND USAGE THEREOF

(75) Inventors: Wen-Jung Wu, Taipei (TW);
Chung-Tsai Lee, Changhua County (TW); Jyh-Wei Chen, Taipei County (TW); Hasiao Chi Peng, Hsinchu County (TW); Li-Ling Liaw, Hsinchu (TW); Gwo-Fang Yuan, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 617 days.

(21) Appl. No.: 12/251,056

(22) Filed: Oct. 14, 2008

(65) Prior Publication Data

US 2009/0093048 A1    Apr. 9, 2009

Related U.S. Application Data

(62) Division of application No. 11/008,728, filed on Dec. 9, 2004, now Pat. No. 7,534,602.

(60) Provisional application No. 60/529,330, filed on Dec. 12, 2003.

(51) Int. Cl.
*C12N 15/00* (2006.01)
(52) U.S. Cl. .................................. 435/320.1; 536/24.1
(58) Field of Classification Search ..................... None
See application file for complete search history.

(56) References Cited

FOREIGN PATENT DOCUMENTS

EP          1325959          9/2003

OTHER PUBLICATIONS

"A New Taxonomy for *Monascus* Species Basedon Cultural and Microscopial Characters" Hawksworth et al.; 1983.
"Transformation of *Monascus purpureus* to hygromycin B resistance with cosmid pMOcosX reduces fertility" Lakrod et al.; 2003.
"Stable transformants of the azaphilone pigment-producing *Monascus purpureus* obtained by protoplast transformation and Agrobacterium-mediated DNA transfer" Campoy et al.; 2003.
J Ind Microbiol Biotechnol (2003) Expression of pigmentation genes following electroporation of albino *Monascus purpureus*.

*Primary Examiner* — Jim Ketter
(74) *Attorney, Agent, or Firm* — Thomas|Kayden

(57) ABSTRACT

Promoters and usage thereof. Two promoters, acuF and hsp promoters, comprise the nucleotide sequences of SEQ ID NO: 1 and 2, respectively.

19 Claims, 7 Drawing Sheets

PROMOTERS AND USAGE THEREOF

CROSS-REFERENCE TO RELATED APPLICATION

This application is a division of U.S. patent application Ser. No. 11/008,728, filed Dec. 9, 2004, which claimed priority to U.S. Provisional Patent Application No. 60/529,330 filed Dec. 12, 2003, which is hereby incorporated by reference.

BACKGROUND

The invention relates to promoters and usage thereof.

Historically, the genus *Monascus* has been wildly used as food additives in China and Asiatic countries. The fermentate is obtained as scarlet to purple red grains which have the original rice grain structure well preserved. In addition, a health promoting effect is ascribed traditionally to the product. The application of *Monascus* in the rice wine manufacture is due to its high content of alpha-amylase which promotes the conversion of starch into glucose. Scientific investigations have confirmed pharmacological effects of *Monascus* fermentate such as Monacolin K, Mevinolin, and the like. The preservative effect of *Monascus* fermentate has also been confirmed.

Studies in this field have focused on the gene products of *Monascus* spp., an increasing interest is that the *Monascus* EST database may provide more information for recombinant DNA technology.

SUMMARY

The inventors have searched *Monascus* EST database of BCRC 38072 deposited in the Food Industry Research and Development Institute. Two genes with high expression rates were obtained and matched as phosphoenolpyruvate carboxykinase (acuF) gene and heat shock protein (hsp) gene. The upstream regions of the two genes were examined and two promoter regions were identified. The invention was then achieved.

Accordingly, an embodiment of the invention provides an isolated DNA molecule comprising a nucleotide sequence of SEQ ID NO: 1 or a nucleotide sequence hybridizable to SEQ ID NO: 1 under stringent conditions. The DNA molecule has promoter activity.

Also provided is a recombinant DNA including a promoter region and a coding region. The promoter region has the nucleotide sequence of SEQ ID NO: 1 or the nucleotide sequence hybridizable to SEQ ID NO: 1 under stringent conditions and the coding region has a nucleotide sequence encoding a desired protein Another embodiment of the invention provides an expression vector comprising a promoter. The promoter has the nucleotide sequence of SEQ ID NO: 1 or the nucleotide sequence hybridizable to SEQ ID NO: 1 under stringent conditions.

Yet another embodiment of the invention provides a DNA molecule comprising a nucleotide sequence of SEQ ID NO: 2 or a nucleotide sequence hybridizable to SEQ ID NO: 2 under stringent conditions. The DNA molecule has promoter activity.

Furthermore, another embodiment of the invention provides a recombinant DNA comprising a promoter region and a coding region. The promoter region has the nucleotide sequence of SEQ ID NO: 2 or the nucleotide sequence hybridizable to SEQ ID NO: 2 under stringent conditions and the coding region has a nucleotide sequence encoding a desired protein.

Moreover, another embodiment of the invention provides an expression vector comprising a promoter having the nucleotide sequence of SEQ ID NO: 2 or the nucleotide sequence hybridizable to SEQ ID NO: 2 under stringent conditions.

BRIEF DESCRIPTION OF THE DRAWINGS

Embodiments of the invention can be more fully understood and further advantages become apparent when reference is made to the following description and the accompanying drawings in which:

FIG. 3A: bright field; FIG. 3B: under fluorescent filter.

FIG. 6A: under light-field; FIG. 6B: under fluorescent filter.

DETAILED DESCRIPTION

Figure 1:
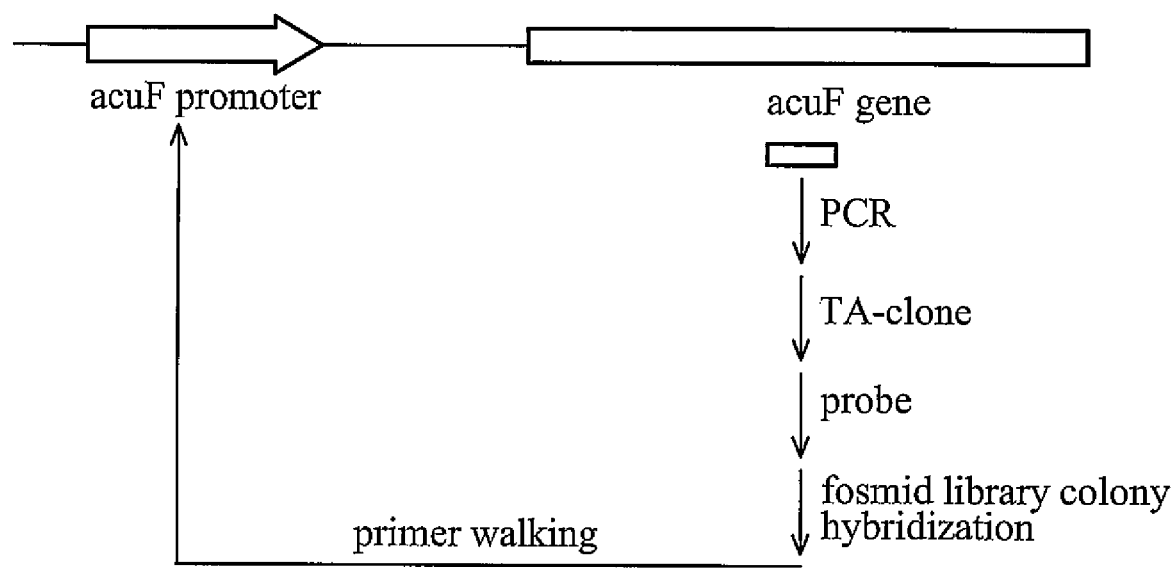
FIG. 1 illustrates the procedures for an embodiment of acuF promoter region.

Two genes with high expression rates were obtained by searching *Monascus* EST database of BCRC 38072 collected in the Food Industry Research and Development Institute and matched as phosphoenolpyruvate carboxykinase (acuF) gene and heat shock protein (Hsp) gene. It was proposed that the two genes are regulated by upstream strong promoters, and the promoters may be used for protein over-expression.

*Monascus* BCRC 38072 was observed as having the characteristics of:

Macroscopic Characteristics:

CYA, 25° C., 7 days. Colonies 25-26 mm diam, mycelium white initially, becoming light reddish orange, reverse deep reddish orange.

MEA, 25° C., 7 days. Colonies 48 mm diam, bright reddish orange, reverse vivid reddish orange.

G25N, 25° C., 7 days. Colonies 28-29 mm diam, deep reddish orange, deep yellowish orange at the centers.

Microscopic Characteristics:

Aleurioconidia arising singly or occasionally in short chains, obpyriform to globose, 10-13×8-10 μm. Cleistothecia globose, 37-72 μm diam. Ascospores hyaline, ellipsoid, 4.6-6.3 (−6.6)×3.3-4.2 μm.

According to the classification system of Hawksworth & Pitt (1983), BCRC 38072 was identified as:

Morphological Characteristics:

BCRC 38072 is between *M. pilosus* and *M. rubber.*

1. BCRC 38072 is similar to *M. pilosus* in colony color and growth rate.

2. BCRC 38072 is similar to *M. ruber* in the morphology of ascospore.

Sequence Analysis:

BCRC 38072, *M. ruber*, and *M. pilosus* share 100% sequence similarity in rDNA ITS fragments and β-tubulin gene.

Species Identification:

BCRC 38072 was temporarily denominated as *Monascus pilosus* K. Sato ex D. Hawksw. & Pitt.

phosphoenolpyruvate carboxykinase (acuF) is important for gluconeogenesis in animals and is persistently and strongly expressed in cells.

Gluconeogenesis in an animal includes the steps of transferring pyruvate into oxaloacetate by pyruvate carboxylase, and transferring oxaloacetate into phosphoenolpyruvate by phosphoenolpyruvate carboxykinase. The reactions are as below.

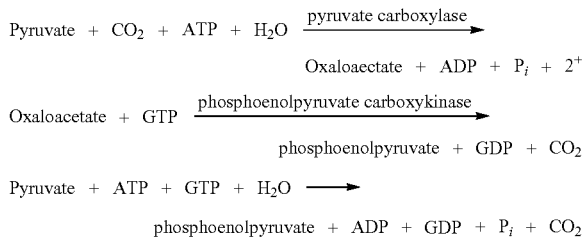

Heat shock protein (Hsp) is a protein family with highly conserved genes and is widespread in prokaryotes and eukaryotes. This protein family includes 4 subfamilies: Hsp 90 (83-90 KDa), Hsp 70 (66-78 KFa), Hsp 60, and small Hsp families classified by their molecular weights. The over-expression of these proteins in an animal is induced by environmental stimuli.

The promoters of acuF and Hsp genes were compared with published database by BLAST, and no similar sequence was found. Recombinant vectors were then prepared by the recombination of acuF or Hsp promoters with pHygEGFP which includes Hph (hygromycin B phosphotransferase) and enhanced green fluorescent protein (EGFP) fusion protein. It has been proved that the two promoters have the activity of opening downstream genes from the observation of EGFP expression using these recombinant vectors.

(I) acuF Promoter

Accordingly, an embodiment of the invention provides an isolated DNA molecule comprising a nucleotide sequence of SEQ ID NO: 1 or a nucleotide sequence hybridizable to SEQ ID NO: 1 under stringent conditions. The DNA sequence has promoter activity. The DNA molecule having promoter activity may comprises from about 117 to about 1116 contiguous nucleotides of SEQ ID NO: 1, particularly from about 367 to about 1116 contiguous nucleotides of SEQ ID NO: 1, more particularly from about 517 to about 1116 contiguous nucleotides of SEQ ID NO: 1. In addition, the DNA molecule is obtained from bacteria or fungi, particularly from *Monascus sp.*, more particularly from *Monascus pilosus, Monascus ruber*, or *Monascus purpureus*. The DNA molecule can be cloned by genetic engineering from the upstream sequence of the start coden of phosphoenolpyruvate carboxykinase (acuF) in BCRC 38072 deposited in the Food Industry Research and Development Institute. The genetic engineering includes gene library construction, colony hybridization, primer walking, or PCR. Moreover, it is easy for those skilled in the art to obtain the DNA sequence or the substantial promoter region by PCR, hybridization, and artificial synthesis according to the DNA sequence disclosed in the invention. The stringent condition for hybridization can be found in EP 1325959 A1 P7 [0036].

Another embodiment of the invention provides a recombinant DNA comprising a promoter region and a coding region. The promoter region comprises the nucleotide sequence of SEQ ID NO: 1, or the nucleotide sequence hybridizable to SEQ ID NO: 1 under stringent conditions. Particularly, the promoter region comprises from about 117 to about 1116 contiguous nucleotides of SEQ ID NO: 1, more particularly, from about 367 to about 1116 contiguous nucleotides of SEQ ID NO: 1, or even from about 517 to about 1116 contiguous nucleotides of SEQ ID NO: 1. The promoter region can be obtained from *Monascus sp*, particularly, from *Monascus pilosus, Monascus ruber*, or *Monascus purpureus*, and can be cloned by genetic engineering from the upstream sequence of the start coden of phosphoenolpyruvate carboxykinase (acuF) in BCRC 38072 deposited in the Food Industry Research and Development Institute. The coding region comprises a nucleotide sequence encoding a desired protein. The desired protein includes enzymes such as protease, polyketide synthase and lipase; transcription factors such as activators and RNA polymerase; and hormone such as insulin and growth factor.

Yet another embodiment of the invention provides an expression vector comprising a promoter having the nucleotide sequence of SEQ ID NO: 1 or the nucleotide sequence hybridizable to SEQ ID NO: 1 under stringent conditions. The promoter is as defined in the promoter region of the embodiment of the recombinant DNA. Material for constructing the embodiment of the expression vector includes a molecule sequence suitable for self-amplification in a host cell or integration into the host chromosome, such as a plasmid, a phage, or a virus. The expression vector selectively includes a nucleotide sequence encoding a desired protein, and the desired protein includes enzymes such as protease, polyketide synthase and lipase; transcription factors such as activator and RNA polymerase; and hormone such as insulin and growth factor.

Another aspect of the invention relates to an expression system comprising the defined expression vector, and a host cell suitable for expressing the desired protein. The vector is transformed into the host cell by transformation. The host cell indicates any cell suitable for expressing the desired protein. Suitable host cells include bacteria, yeasts, animal cells, insect cells, plant cells, or filamentous fungi. The filamentous fungi can be *Monascus sp.*, particularly *Monascus pilosus, Monascus rubber*, or *Monascus purpureus*, more particularly BCRC38072. Transformation can be completed by applying a transformation method for filamentous fungi belonging to the genus *Aspergillus* using the standing known host-vector system. See EP 1325959 A1 P5 [0022].

The invention also relates to a transformant comprising a nucleotide sequence of a) SEQ ID NO: 1, b) from about 117 to about 1116 contiguous nucleotides of SEQ ID NO: 1, c) from about 367 to about 1116 contiguous nucleotides of SEQ ID NO: 1, or d) from about 517 to about 1116 contiguous nucleotides of SEQ ID NO: 1, or a nucleotide sequence hybridizable to the nucleotide sequence defined above under stringent conditions. The transformant further comprises a nucleotide sequence encoding a desired protein.

The invention also relates to a method for the expression of a protein. The method comprises culturing an embodiment of a transformant which includes a nucleotide sequence encoding a desired protein in a medium, producing and accumulating the desired protein from the transformant to the medium, and collecting the desired protein from the medium.

(II) Hsp Promoter

An embodiment of the invention provides an isolated DNA molecule comprising a nucleotide sequence of SEQ ID NO: 2 or a nucleotide sequence hybridizable to SEQ ID NO: 2 under stringent conditions. The DNA molecule has promoter activity. The DNA molecule having promoter activity may comprises from about 443 to about 1478 contiguous nucleotides of SEQ ID NO: 2, particularly from about 759 to about 1478 contiguous nucleotides of SEQ ID NO: 2, more particularly from about 982 to about 1478 contiguous nucleotides of SEQ ID NO: 2. The DNA molecule can be obtained from bacteria or fungi, particularly from *Monascus sp.*, more particularly from *Monascus pilosus, Monascus ruber*, or *Monascus purpureus*. The DNA was cloned by genetic engineering from the upstream sequence of the start coden of heat shock protein (hsp) in BCRC38072 deposited in the Food Industry Research and Development Institute. The genetic engineering includes gene library construction, colony hybridization, shotgun, and PCR. Moreover, the DNA sequence or the substantial promoter region is obtainable for those skilled in the art by PCR, hybridization, and artificial synthesis according to the sequence disclosed in the invention. The stringent conditions for hybridization can be found in EP 1325959 A1 P7 [0036].

Another aspect of the invention provides a recombinant DNA comprising a promoter region and a coding region. The promoter region comprises a nucleotide sequence of SEQ ID NO: 2 or a nucleotide sequence hybridizable to SEQ ID NO: 2 under stringent conditions. Particularly, the promoter region comprises from about 443 to about 1478 contiguous nucleotides of SEQ ID NO: 2, more particularly from about 759 to about 1478 contiguous nucleotides of SEQ ID NO: 2, or even from about 982 to about 1478 contiguous nucleotides of SEQ ID NO: 2. The DNA molecule can be obtained from bacteria or fungi, particularly from *Monascus sp.*, more particularly from *Monascus pilosus, Monascus ruber*, or *Monascus purpureus*. The DNA was cloned by genetic engineering from the upstream sequence of the start coden of heat shock protein (hsp) in BCRC38072 deposited in the Food Industry Research and Development Institute. The coding region comprises a nucleotide sequence encoding a desired protein. The desired protein includes enzymes such as protease, polyketide synthase and lipase; transcription factors such as activator and RNA polymerase; and hormone such as insulin and growth factor.

Yet another embodiment of the invention provides an expression vector comprising a promoter having the nucleotide sequence of SEQ ID NO: 2 or the nucleotide sequence hybridizable to SEQ ID NO: 2 under stringent conditions. The promoter is as defined in the promoter region of the embodiment of the recombinant DNA. Material for constructing the embodiment of the expression vector includes a molecule sequence suitable for self-amplification in a host cell or integration into the host chromosome, such as a plasmid, a phage, or a virus. The expression vector selectively includes a nucleotide sequence encoding a desired protein, and the desired protein includes enzymes such as protease, polyketide synthase and lipase; transcription factors such as activator and RNA polymerase; and hormone such as insulin and growth factor.

Another aspect of the invention relates to an expression system comprising the defined expression vector, and a host cell suitable for expressing the desired protein. The expression vector is transformed into the host cell by transformation. The host cell includes any cell suitable for expressing the desired protein. Suitable host cells include bacteria, yeasts, animal cells, insect cells, plant cells, or filamentous fungi. The filamentous fungi can be *Monascus sp.*, particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1325959 A1 P5 [0022].

The invention also relates to a transformant comprising a nucleotide sequence of a) SEQ ID NO: 2, b) from about 443 to about 1478 contiguous nucleotides of SEQ ID NO: 2, c) from about 759 to about 1478 contiguous nucleotides of SEQ ID NO: 2, d) from about 982 to about 1478 contiguous nucleotides of SEQ ID NO: 2, or a nucleotide sequence hybridizable to the nucleotide sequence defined above under stringent conditions. The transformant further comprises a nucleotide sequence encoding a desired protein.

The invention also relates to a method for the expression of a protein. The method comprises culturing a transformant which includes a nucleotide sequence encoding a desired protein in a medium, producing and accumulating the desired protein from the transformant to the medium, and collecting the desired protein from the medium.

Practical examples are described herein.

EXAMPLE 1 acuF Promoter

1. Materials:
   (1) Host cell: *Monascus* BCRC 38702 (Food Industry Research and Development institute).
   (2) Competent cell: ECOS™ *E. Coli* competent cells DH5α (Yeastern Biotech Co., Ltd.)
   (3) Plasmid: pHygEGFP (BD Biosciences), pGEM®-T Easy Vector (PROM EGA).
   (4) Media:
     a. For *E. coli*: LB Broth (USB), agar (USB).
     b. For *Monascus sp.* and *Neurospora crassa*: PDA (DIFICO), PDB (DIFICO), Vogel's medium (see *), and top agar.
   (5) Antibiotics: Ampicillin, Hygromycin B (SIGMA).
   *Vogel's medium
   1. Trace elements solution: 5 g citric acid□$H_2O$, 5 g $ZnSO_4$□$7H_2O$, 1 g $Fe(NH_4)_2(SO_4)_2$□$6H_2O$, 250 mg $CuSO_4$□$5H_2O$, 50 mg $MnSO_4$□$H_2O$, 50 mg $H_3BO_3$, 50 mg $Na_2MoO_4$□$2H_2O$ in 95 ml dd$H_2O$. The Final volume: 100 ml.
   2. Biotin solution: 5 mg biotin (Sigma) in 199 ml 5% ethanol.
   3. 50× Vogel's salt stock: 150 g $Na_3$ citrate□$5H_2O$, 250 g $KH_2PO_4$, 100 g $NH_4NO_3$, 10 g $MgSO_4$□$7H_2O$, 5 g $CaCl_2$□$2H_2O$ (slowly dissolved in 20 ml $H_2O$ previously) in 750 ml dd$H_2O$, add 5 ml trace elements solution and 5 ml biotin solution. The final volume: 1 liter. After filtration, sterilization, the solution is stored at RT.
   4. Modified Vogel's medium: 1% Glucose in 1× Vogel's salt.

Figure 2:
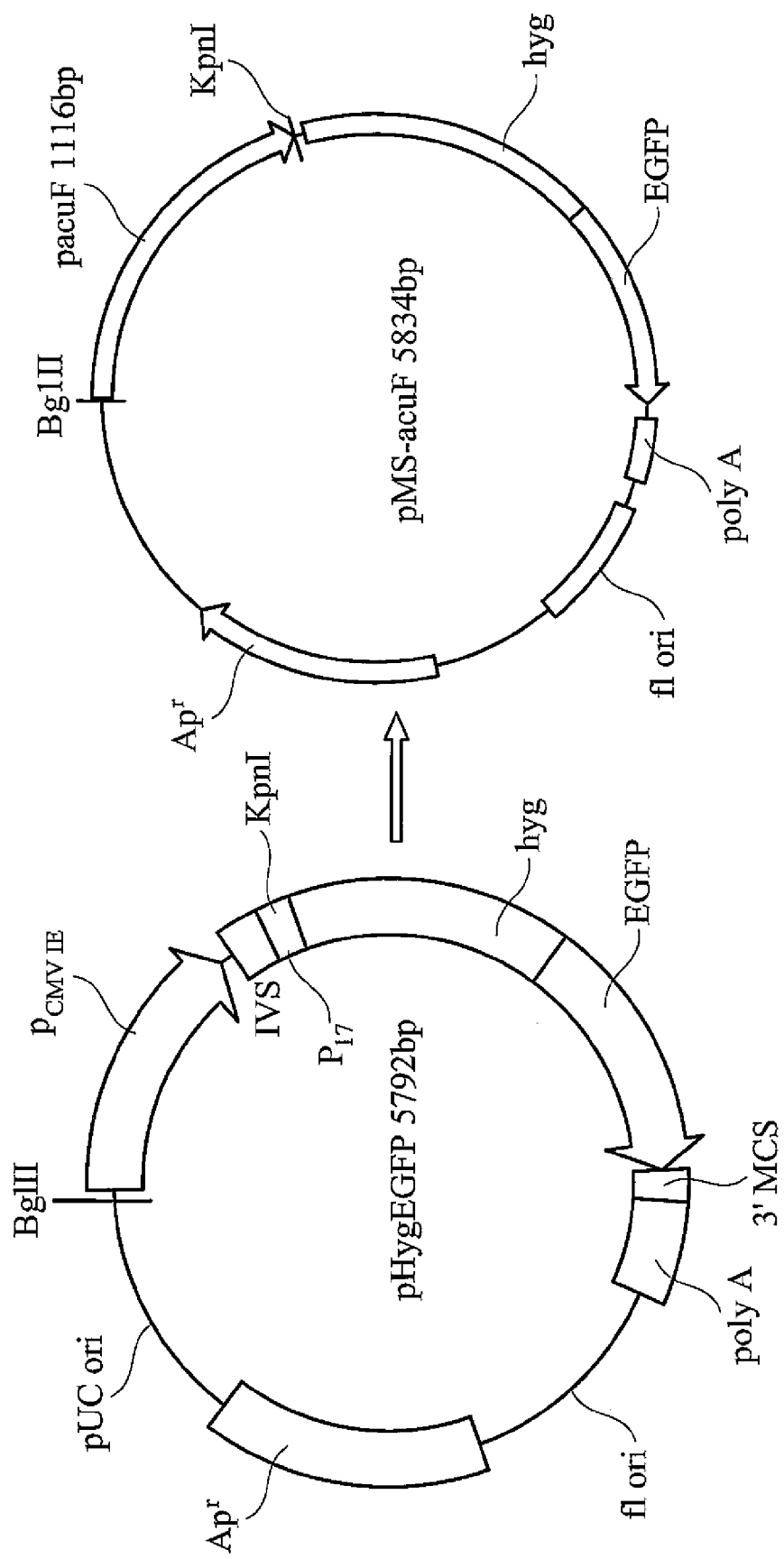
FIG. 2 illustrates the recombinant vector of the embodiment of acuF promoter region. The embodiment of acuF promoter region was cloned into the vector pHygEGFP to be the recombinant vector pMS-acuF.
Figure 3A:
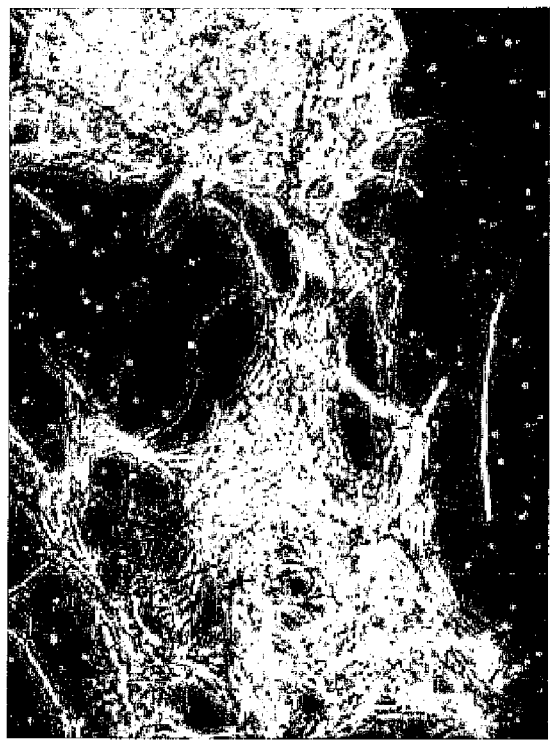
FIGS. 3A and 3B illustrate the EGFP expression after pMS-acuF transformation.
Figure 3B:

2. Procedures:
   The procedures for acuF promoter are as shown in FIG. 1. A highly expressed gene Contig ID: MPTC00008457 was found from *Monascus* BCRC 38072 EST database in the Food Industry Research and Development Institute (FIRDI) and identified as phosphoenolpyruvate carboxykinase (acuF) gene. The gene was speculated as being regulated by a strong promoter. A probe of 465 bp was then designed according to the 5' terminal sequence of acuF gene. The acuF probe was amplified by PCR from *Monascus* chromosome. After that, the PCR product was ligated to pGEM®-T Easy Vector, and the acuF probe was obtained by labeling with DIG (Digoxigenin). Colony hybridization was performed using the probe in fosmid library of *Monascus* BRCR 38072, and fosmid containing acuF gene was screened. The fosmid mpf01014A4 was sequenced by primer walking, and the tentative promoter sequence at upstream of acuF gene was located. The tentative promoter sequence of 1116 bp was successfully sequenced and then compared with BLAST database but no similar gene was found. The tentative acuF promoter sequence of 1116 bp was ligated into pHygEGFP by restriction sites of BglII and KpnI and the resulting plasmid was designated pMS-a1 as shown in FIG. 2 (the right one). pMS-a1 was transformed into *Monascus* and EGFP expression was observed as shown in FIG. 3 where FIG. 3A is bright field and FIG. 3B under fluorescent filter. The results confirmed that the tentative acuF promoter has promoter activity. It is to be noted that pMS-a1 transformed in to *E. coli* DH5α (as strain *Escherichia coli* DH5α has been deposited as PTA-5687 in the American Type Culture Collection, located at 10801 University Blvd., Manassas, Va. 20110-2209, on Dec. 10, 2003. The procedures are described in details as below.

A. Obtaining Acuf Probe Gene Fragment acuF probe was cloned by Polymerase Chain Reaction (PCR) from BCRC38072.

Primers were designed according to *Monascus* EST database.

```
Forward primer:
5'-TGTTAATAGGACCGCCCTGC-3'    (SEQ ID NO: 3)

Reverse primer:
5'-AGTATGCGGTCAGAGCACC-3'     (SEQ ID NO: 4)
```

The reaction condition was listed below.

| | DNA Template (10 ng/μl) | Forward primer (10 μM) | Reverse primer (10 μM) | Polymersae taq | dNTP 10 mM | 10 × buffer | Mg$^{2+}$ | H$_2$O | Total |
|---|---|---|---|---|---|---|---|---|---|
| μl | 2 | 2 | 2 | 1 | 2 | 10 | 13 | 50 | 100 |
| | | | Cycle | 94° C. | 53° C. | 72° C. | | 4° C. | |
| 1$^{st}$ round | | 1 | | 7 min | | | | | |
| 2$^{nd}$ round | | 30 | | 1 min | 30 s | 30 s | | | |
| 3$^{rd}$ round | | 1 | | | | 15 min | | ∞ | |

After the reaction, the amplified fragments were extracted by equal volume of phenol/chloroform (24/25) and precipitated by 1/10 volume of 3M sodium acetate and 2× volume of 100% ethanol. The precipitated DNA was washed by 70% ethanol, centrifuged, and air-dried. The product was dissolved in ddH$_2$O and stored at −20° C.

B. Recombination of Plasmid TA-acuF

The PCR product of acuF probe was purified and collected. The DNA was mixed with pGEM®-T Easy Vector in a ratio of 3:1. 1 μl of T4 DNA ligase and 10× ligation buffer were added and suitable amount of ddH$_2$O was added to be a final volume of 10 μl. The ligation reaction was performed at room temperature for 1 hour. After ligation, 5 μl of ligation product was added to 100 μl of ECOS™ *E. coli* competent cells DH5α for transformation. Recombinant plasmid of 3483 bp was screened and confirmed by PCR. The recombinant plasmid TA-acuF was obtained.

C. Obtaining the acuF Promoter Fragment

AcuF promoter gene was cloned by Polymerase Chain Reaction (PCR) from fosmid: mpf01014A4.

The primers and reaction condition used here are listed below.

```
Forward primer:
                              (SEQ ID NO: 6)
5'-GAAGATCTCTCGTATGTTGTGTGGAATTGTGAGC-3'

Reverse primer:
                              (SEQ ID NO: 7)
5'-ATGGTACCTGTTTCTGAGTGAGGTCGAGTG-3'
```

| | DNA Template (10 ng/μl) | Forward primer (10 μM) | Reverse primer (10 μM) | Polymersae taq | dNTP 10 mM | 10 × buffer | Mg$^{2+}$ | H$_2$O | Total |
|---|---|---|---|---|---|---|---|---|---|
| μl | 2 | 2 | 2 | 1 | 2 | 10 | 13 | 50 | 100 |
| | | | cycle | 94° C. | 59° C. | 72° C. | | 4° C. | |
| 1$^{st}$ round | | 1 | | 7 min | | | | | |
| 2$^{nd}$ round | | 30 | | 1 min | 30 s | 1 min | | | |
| 3$^{rd}$ round | | 1 | | | | 15 min | | ∞ | |

After the reaction, the amplified fragments were extracted by equal volume of phenol/chloroform (24/25) and precipitated by 1/10 volume of 3M sodium acetate and 2× volume of 100% ethanol. The precipitated DNA was washed by 70% ethanol, centrifuged, and air-dried. The product was dissolved in ddH$_2$O and stored at −20° C.

D. Preparation of Recombinant pMS-a1

The PCR product of promoter acuF and cloning vector pHygEGFP were separately digested by BglII and KpnI for 4 hours. The resulting fragments were separated by DNA electrophoresis and extracted by QIAquick® GEL EXTRACTION KIT. The vector and promoter acuF were mixed in a ratio of 1:3 and added to ddH$_2$O for a final volume of 10 µl. Ligation was performed at 16° C. for 4 hours. After ligation, 5 µl of the reaction was added into 100 µl of ECOS™ E. coli competent cells DH5α for transformation. Plasmid with 6.1 kb was screened and confirmed by PCR. The recombinant plasmid pMS-a1 was obtained.

E. Preparation of Monascus Protoplast

Monascus spore solution was plated onto PDA slant and incubated at 30° C. for 5-7 days. The spores were stripped with sterilized water and filtrated by two-layer sterilized miracloth to remove the hyphae and the agar. The filtrated spores were counted under light microscopy by a hemocytometer. Spores were harvested in a concentration of 10$^7$ spores/ml in 50 ml modified Vogel's medium and incubated at 30° C. under 200 rpm vibration for 16-18 hours. Germinated spores were filtrated by two-layer miracloth and washed with sterilized water. The hyphae were rinsed with enzyme digestion buffer.

The hyphae on the miracloth was washed out by 10 ml of enzyme digestion buffer and added to 5 ml of enzyme mixture. The mixture was vortexed at room temperature for 30 min. The degradation of the cell wall was observed under light microscopy every ten min during the vortex until protoplasts were released from 90% of the hyphae. The mixture was filtrated with two-layer miracloth, and the filtrated solution was centrifuged at 1500 rpm at 4° C. for 15 min to collect the protoplasts. The supernatant was discarded, and the pellet was washed with enzyme digestion buffer twice and then with STC twice. 1.5 ml of STC, 20 µl of DMSO and 0.4 ml of PTC were added in the solution and the protoplasts were counted under microscopy. The protoplasts were distributed in a concentration of 10$^7$ protoplasts/ml and stored at −80° C.

F. Transformation

The protoplasts were washed with STC twice and centrifuged at 1500 rpm at 4° C. for 15 min. The supernatant was discarded, and the protoplast pellet was resolved in 50 µl of STC. 1-10 µg plasmid DNA was added into the solution. The electroporation was performed under the condition of 200 Ohms, 25 µF, 0.7 KV. 1 ml of regeneration buffer was then added into the mixture, and the mixture was placed at 30° C. overnight. 10 ml of top agar at 50° C. containing 30 µg/ml of hygromycin B wad added to the mixture, and the mixture was then poured on a top agar containing 30 µg/ml of hygromycin B. After 3-5 days of cultivation at 30° C., the transformants can be observed.

G. Screening and Confirmation of the Transformants (1) Few hyphae and spores of the transformant were sampled to place on a slide, a drop of distilled water was added, and the slide was covered with a cover slide. The sample was then observed under light microscopy. Green fluorescence of hyphae and spore were observed under GFP filter (Ex. 430-510 nm; Em. 475-575 nm).

(2) The transformant was grown in PDB (potato dextrose broth) at 30° C. with 200 rpm vibration for 5-10 days. The culture was homogenized and the chromosomal DNA was extracted. PCR was performed with HPH-EGFP specific primer and a product of 1740 bp was obtained.

H. Confirmation of the Smallest Fragment Having Promoter Activity

To further confirm the smallest fragment of acuF promoter (1116 bp) having promoter activity, PCR products having 1000 bp, 750 bp, 600 bp, and 500 bp fragments of acuF promoter were prepared from pMS-a1. The primers for the preparation of these PCR products are listed below.

```
1000 bp:
Forward primer:
acuF-B2
gaagatctTGTCGATGCAATCGGGCAATCC    (SEQ ID NO: 13)

Reverse primer:
acu F-KpnI
atggtacctGTTTCTGAGTGAGGTCGAGTG    (SEQ ID NO: 14)

750 bp:
Forward primer:
acuF-B3
gaagatctTGATGATTGGGATCGGACTCGG    (SEQ ID NO: 15)

Reverse primer:
acu F-KpnI
atggtacctGTTTCTGAGTGAGGTCGAGTG    (SEQ ID NO: 14)

600 bp:
Forward primer:
acuF-B4
gaagatctTGCGGATCCGAGGATAAAAC      (SEQ ID NO: 16)

Reverse primer:
acu F-KpnI
atggtacctGTTTCTGAGTGAGGTCGAGTG    (SEQ ID NO: 14)

500 bp:
Forward primer:
acuF-B5
gaagatctCCCGGTATTGTCCGAGGCTC      (SEQ ID NO: 17)

Reverse primer:
acu F-KpnI
atggtacctGTTTCTGAGTGAGGTCGAGTG    (SEQ ID NO: 14)
```

The PCR products having 1000 bp, 750 bp, 600 bp, and 500 bp fragments of acuF promoter were cloned into pMS and designated as pMS-a2, pMS-a3, pMS-a4, and pMS-a5. These plasmids were then transformed into Monascus BCRC 38072 and screened by PDA plate containing Hyg$^r$ 30 ug/ml. The results are shown as below.

| Monascus BCRC38072 | promoter size | Hyg 30 ug/ml[1] | Fluorescence[2] |
|---|---|---|---|
| pMS-a1 | 1116 bp | R | + |
| pMS-a2 | 1000 bp | R | + |
| pMS-a3 | 750 bp | R | + |
| pMS-a4 | 600 bp | R | + |
| pMS-a5 | 500 bp | N.R. | N.D. |

[1]R: resistance; N.R.: non-resistance.
[2]+: positive; −: negative.
N.D.: not detected.

The smallest fragment having promoter activity is 600 bp. The fluorescence can be detected in the transformant containing the fragment of 600 bp.

These plasmids were also transformed into Monascus pilosus BCRC 31527 and screened by PDA plate containing Hyg$^r$ 50 ug/ml. The results are shown as below.

| *Monascus pilosus* BCRC31527 | Promter size | Hyg 50 ug/ml[1] | Fluorescence[2] |
|---|---|---|---|
| pMS-a3 | 750 bp | R | + |
| pMS-a4 | 600 bp | R | + |
| pMS-a5 | 500 bp | N.R. | N.D. |

[1]R: resistance; N.R.: non-resistance.
[2]+: positive; −: negative.
N.D.: not detected.

The smallest fragment having promoter activity is 600 bp. The fluorescence can be detected in the transformant containing the fragment of 600 bp.

These plasmids were also transformed into *Neurospora crassa* BCRC 32685 and screened by PDA plate containing Hyg$^r$ 50 ug/ml. The results are shown as below.

| *Neurospora crassa* BCRC32685 | Promter size | Hyg 200 ug/ml[1] |
|---|---|---|
| pMS-a3 | 750 bp | R |
| pMS-a4 | 600 bp | R |
| pMS-a5 | 500 bp | N.D. |

[1]R: resistance; N.R.: non-resistance.
N.D.: not detected.

The results also confirmed that the smallest fragment having promoter activity is 600 bp.

The smallest fragments of acuF promoter having promoter activity was confirmed as 600 bp (SEQ ID NO: 18) and can be expressed in *Monascus* BCRC 38072, *Monascus pilosus* BCRC31527, and *Neurospora crassa* BCRC326.

EXAMPLE 2

Hsp Promoter

1. Materials:
   (1) Host cell: *Monascus* BCRC 38702 (the Food Industry Research and Development institute).
   (2) Competent cell: ECOS™ *E. Coli* competent cells DH5α (Yeastern Biotech Co., Ltd.)
   (3) Plasmid: pHygEGFP (BD Biosciences), pGEM®-T Easy Vector (PROMEGA).
   (4) Media:
      a. For *E. coli*: LB Broth (USB), agar (USB).
      b. For *Monascus sp.* and *Neurospora crassa*: PDA (DIFICO), PDB (DIFICO), Vogel's medium (as listed above), and top agar.
   (5) Antibiotics: Ampicillin, Hygromycin B (SIGMA).

Figure 4:
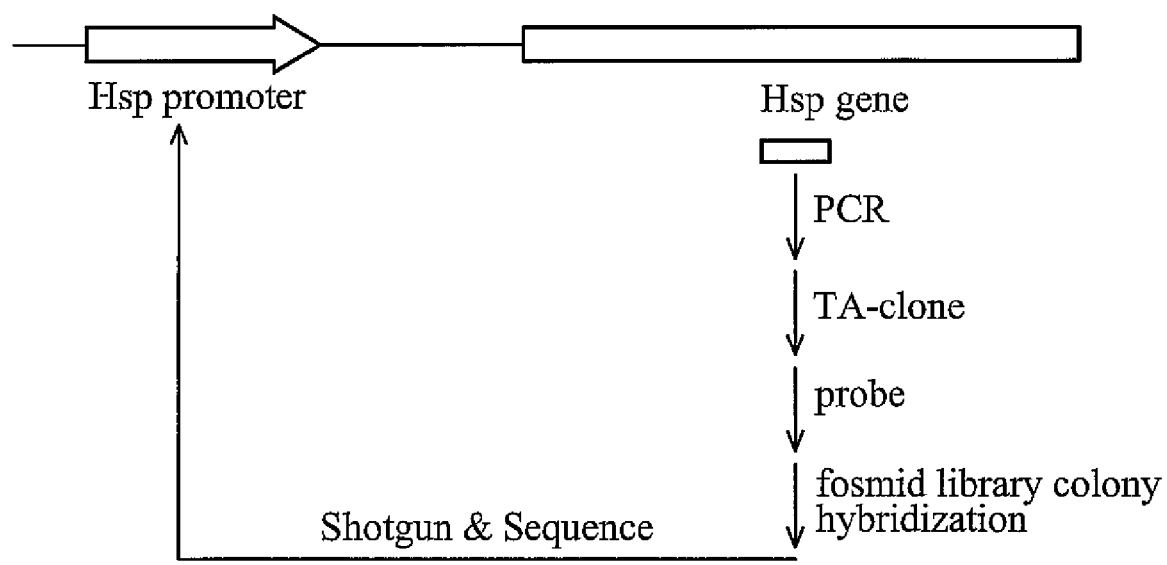
FIG. 4 illustrates the procedures for an embodiment of Hsp promoter region.

2. Procedures:
The procedures for Hsp promoter are as shown in FIG. 4. Heat shock protein (Hsp) obtained from *Monascus* BCRC 38072 cDNA library was found highly expressed after 3 day-incubation at 25° C. A probe for Hsp was designed according to the 5' terminal of Hsp gene sequence and amplified from *Monascus* chromosome by PCR. The PCR product was ligated to pGEM®-T Easy Vector, and the resulting sequence was designated as TA-Hsp. The TA-Hsp was labeled with DIG (Digoxigenin) and amplified by PCR to produce a probe with DIG labeling. Colony hybridization was performed in fosmid library of *Monascus* BCRC 38072 using the probe, and the fosmid containing Hsp was found. The Hsp gene sequence and 5' region were located from the sequencing result of the fosmid using shotgun.

Figure 5:
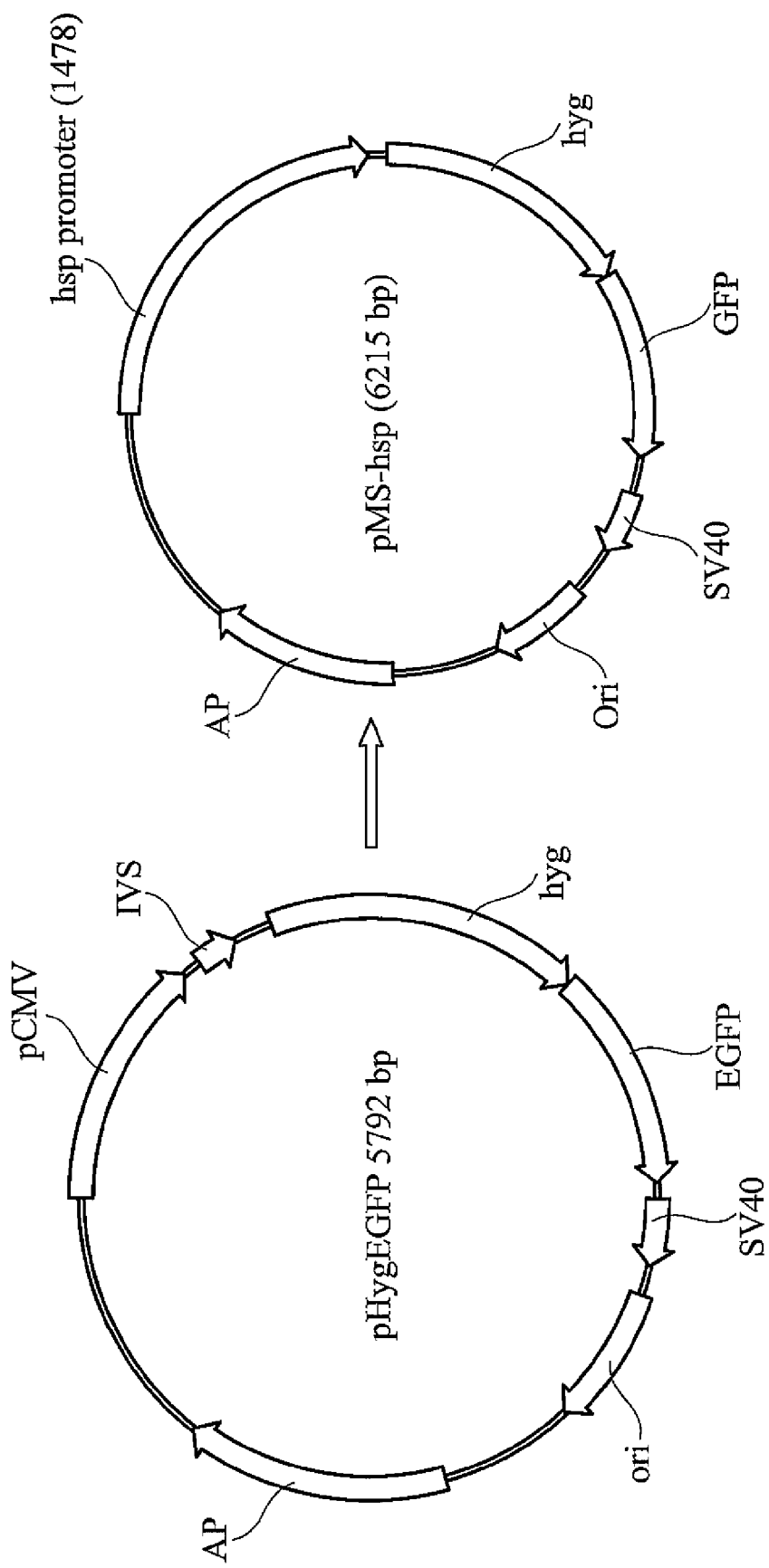
FIG. 5 illustrates the recombinant vector of the embodiment of Hsp promoter region. The embodiment of Hsp promoter region was cloned into the vector pHygEGFP to be pMS-hsp.
Figure 6A:
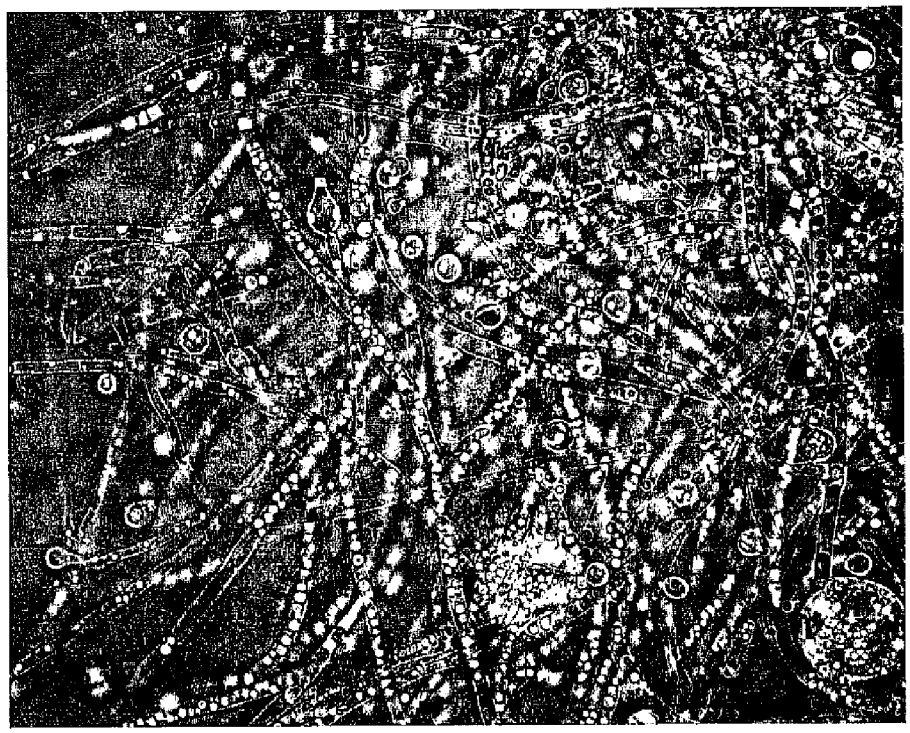
FIGS. 6A and 6B illustrate the EGFP expression after pMS-hsp transformation.
Figure 6B:
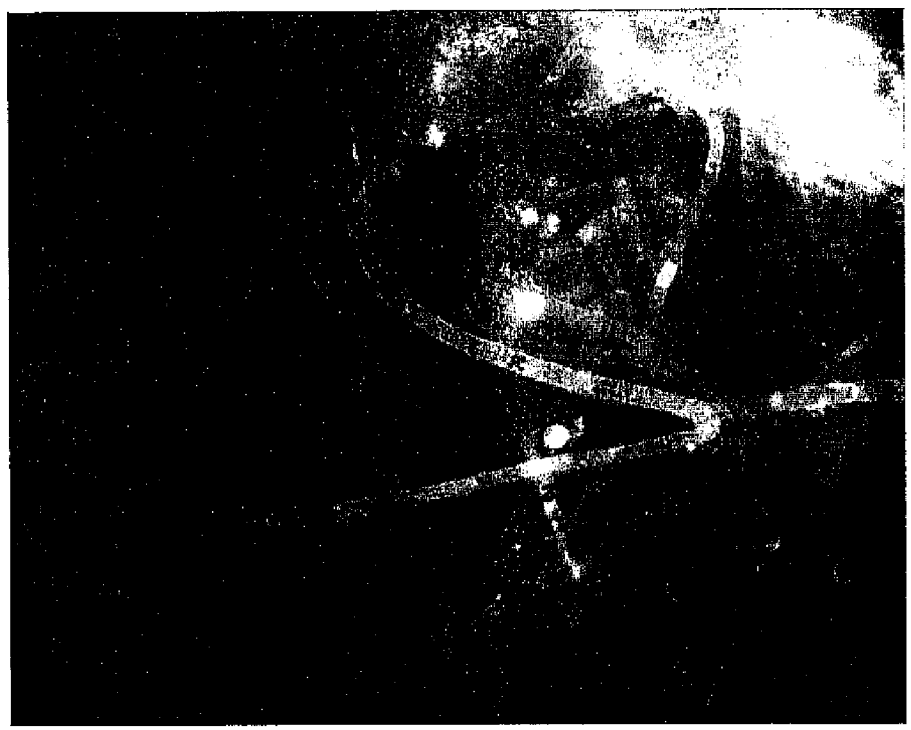
Figure 7:
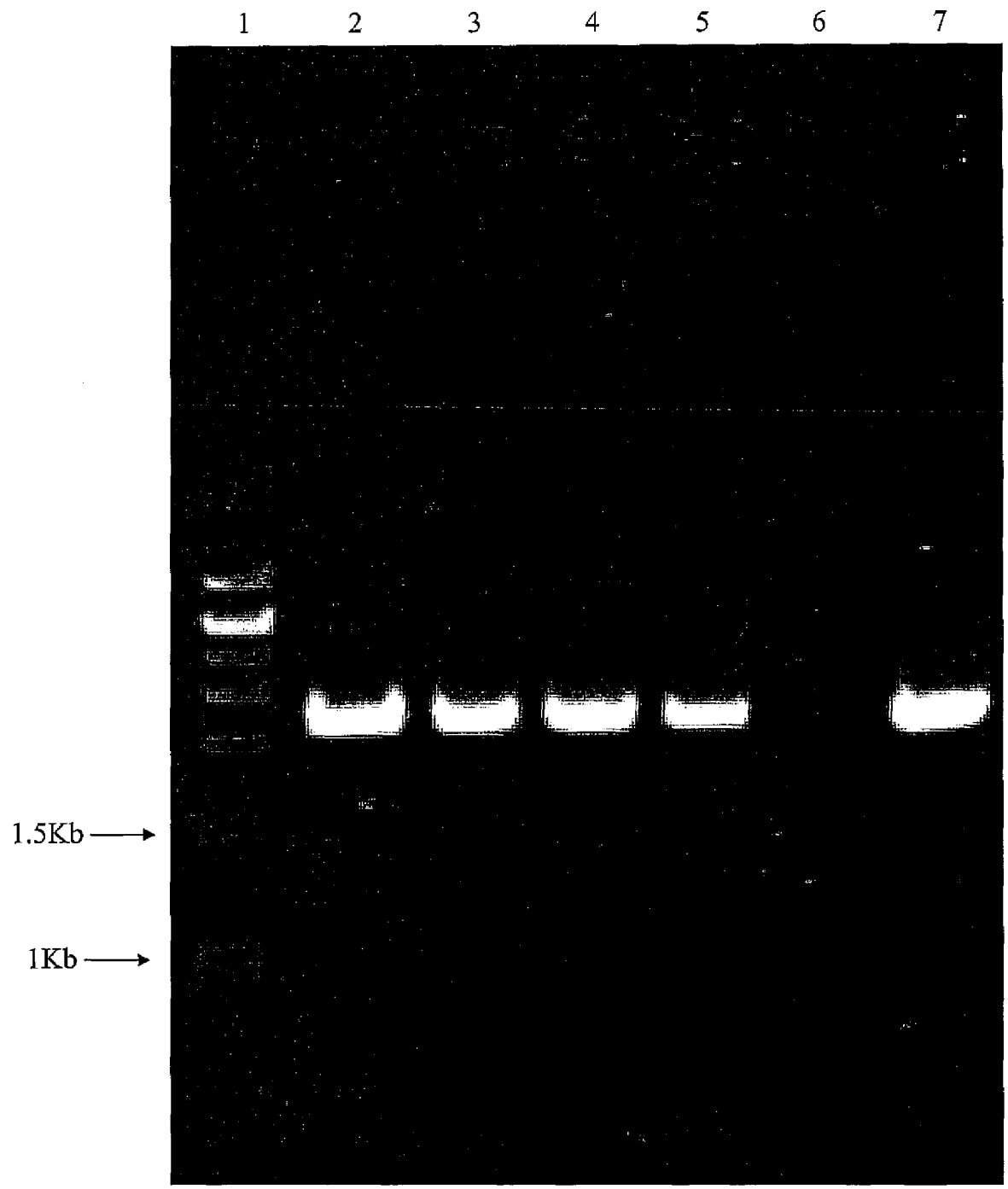
FIG. 7 illustrates the electrophoresis of the PCR produce. Lane 1: 1 kb marker (Bio-1kb™ DNA ladder); lanes 2-5 transformants No. 1-4; lane 6: BCRC 38072 wild-type, (−) control; and lane 7: pHygEGFP, (+) control.

Primers were designed from the 5' region of Hsp gene. A region of 1478 bp was amplified from *Monascus* chromosome by PCR. The region of 1478 bp was digested at BglII and XhoI restriction sites and ligated to a commercialized vector pHygEGFP. The resulting plasmid was designated as pMS-hsp as shown in FIG. 5 (the right one). The vector pMS-hsp was transformed to *Monascus* BCRC 38072 and the transformants were screened by Hyrgromycin B. The observation of EGFP expression in the obtained transformants under fluorescent microscopy indicates that the region of 1478 bp has promoter activity as shown in FIG. 6. FIG. 6A is under light field and FIG. 6B is under fluorescent filter. The chromosomal DNA of the transformant of *Monascus* BCRC38072 was extracted by QIAGEN DNeasy® Plant kit and used as a template for PCR reaction with HPH-EGFP specific primers. A PCR product of 1740 bp was obtained as shown in FIG. 7. Lane 1 indicates 1 kb marker (Bio-1 Kb™ DNA Ladder), lanes 2-5 transformants no. 1-4, lane 6 BCRC 38072 wild-type, (−) control, and lane 7 pHygEGFP, (+) control. It is to be noted that pMS-hsp transformed to *E. coli* DH5α (as strain *Escherichia coli* DH5α: pMS-Hsp) has been deposited as PTA-5688 in the American Type Culture Collection, located at 10801 University Blvd., Manassas, Va. 20110-2209, on Dec. 10, 2003. The procedures are described in details as below.

A. Obtaining Hsp Probe Gene Fragment

Hsp probe was cloned by Polymerase Chain Reaction (PCR) from *Monascus* BCRC38072.

Primers were designed according to *Monascus* EST database.

```
Forward primer:
mptc3161-A:
5'-GCTTATCTCCAATGCCTCCG -3'    (SEQ ID NO: 8)

Reverse primer:
mptc3161-B:
5'-CAAGGTCTCGCTCGTTAC-3'       (SEQ ID NO: 9)
```

The reaction condition was listed below.

| | DNA Template (10 ng/μl) | Forward primer (10 μM) | Reverse primer (10 μM) | Polymersae taq | dNTP 10 mM | 10 × buffer | Mg$^{2+}$ | H$_2$O | Total |
|---|---|---|---|---|---|---|---|---|---|
| μl | 2 | 2 | 2 | 1 | 2 | 10 | 13 | 50 | 100 |
| Cycle | | | | 94° C. | 55° C. | 72° C. | | 4° C. | |
| 1$^{st}$ round | | 1 | | 7 min | | | | | |
| 2$^{nd}$ round | | 30 | | 1 min | | 30 s | 30 s | | |
| 3$^{rd}$ round | | 1 | | | | 15 min | | ∞ | |

After the reaction, the amplified fragments were extracted by equal volume of phenol/chloroform (24/25) and precipitated by 1/10 volume of 3M sodium acetate and 2× volume of 100% ethanol. The precipitated DNA was washed by 70% ethanol, centrifuged, and air-dried. The product was dissolved in ddH$_2$O and stored at −20° C.

B. Recombination of Plasmid TA-Hsp

The PCR product of Hsp probe was purified and collected. The DNA was mixed with pGEM®-T Easy Vector in a ratio of 3:1. 1 µl of T4 DNA ligase and 10× ligation buffer were added and suitable amount of ddH$_2$O was added to produce a final volume of 10 µl. The ligation reaction was performed at room temperature for 1 hour. After ligation, 5 µl of ligation product was added into 100 µl of ECOS™ E. coli competent cells DH5α for transformation. Recombinant plasmid of 3482 bp was screened and confirmed by PCR. The recombinant plasmid TA-Hsp was obtained.

C. Obtaining the Hsp Promoter Fragment

Hsp promoter primers were designed from *Monascus* EST database, and the Hsp promoter gene was cloned by Polymerase Chain Reaction (PCR) from BCRC 38072.

The primers and reaction condition used here are listed below.

```
Forward primer:
Mps17-9259-F:
5'-AGTGGCAGCCAACCCTCACC -3'        (SEQ ID NO: 11)

Reverse primer:
Mps17-7782-R:
5'-CGGGCTGATAGAGCAGATAGATAGATG -3' (SEQ ID NO: 12)
```

| | DNA Template (10 ng/µl) | Forward primer (10 µM) | Reverse primer (10 µM) | Polymersae taq | dNTP 10 mM | 10 × buffer | Mg$^{2+}$ | H$_2$O | Total |
|---|---|---|---|---|---|---|---|---|---|
| µl | 2 | 2 | 2 | 1 | 2 | 10 | 13 | 50 | 100 |

| | Cycle | 94° C. | 60° C. | 72° C. | | 4° C. | | | |
|---|---|---|---|---|---|---|---|---|---|
| 1$^{st}$ round | 1 | 7 min | | | | | | | |
| 2$^{nd}$ round | 30 | 1 min | 30 s | 1 min | | | | | |
| 3$^{rd}$ round | 1 | | | 15 min | | ∞ | | | |

After the reaction, the amplified fragments were extracted by equal volume of phenol/chloroform (24/25) and precipitated by 1/10 volume of 3M sodium acetate and 2× volume of 100% ethanol. The precipitated DNA was washed by 70% ethanol, centrifuged, and air-dried. The product was dissolved in ddH$_2$O and stored at −20° C.

D. Preparation of Recombinant pMS-hsp

The PCR product of Hsp promoter and cloning vector pHygEGFP were separately digested by BglII and XhoI for 16 hours. The resulting fragments were separated by DNA electrophoresis and extracted by QIAquick® GEL EXTRACTION KIT. The vector and Hsp promoter were mixed in a ratio of 1:3, and ddH$_2$O was added for a final volume of 10 µl. Ligation was performed at 16° C. for 16 hours. After ligation, 5 µl of the reaction was added into 100 µl of ECOS™ E. coli competent cells DH5α for transformation. Plasmid with 6215 bp was screened and confirmed by PCR. The recombinant plasmid pMS-hsp was obtained.

E. Preparation of *Monascus* Protoplast

*Monascus* spore solution was plated onto a PDA slant and incubated at 30° C. for 5-7 days. The spores were stripped with sterilized water and filtrated by two-layer sterilized miracloth to remove the hyphae and the agar. The filtrated spores were counted under light microscopy by a hemocytometer. Spores were harvested in a concentration of 10$^7$ spores/ml in 50 ml modified Vogel's medium and incubated at 30° C. under 200 rpm vibration for 16-18 hours. Germinated spores were filtrated by two-layer miracloth and washed by sterilized water. The germinated spores were rinsed with enzyme digestion buffer.

The hyphae on the miracloth was washed out by 10 ml of enzyme digestion buffer and added to 5 ml of enzyme mixture. The mixture was shaked at room temperature for 30 min. The degradation of the cell wall was observed under light microscopy every ten min. shake until 90% protoplast were released from the hyphae. The mixture was filtrated with two-layer miracloth and the filtrated solution was centrifuged under 1500 rpm at 4° C. for 15 min to collect the protoplasts. The supernatant was discarded and the pellet was washed with enzyme digestion buffer twice and then with STC twice. 1.5 ml of STC, 20 µl of DMSO and 0.4 ml of PTC were added to the solution and the protoplasts were counted under microscopy. The protoplasts were distributed in a concentration of 10$^7$ protoplasts/ml and stored at −80° C.

F. Transformation

The protoplasts were washed with STC twice and centrifuged under 1500 rpm at 4° C. for 15 min. The supernatant was discarded, and the protoplast pellet was resolved in 50 µl of STC. 1-10 µg plasmid DNA was added into the solution. The electro-transformation was performed under the condition of 200 Ohms, 25 µF, 0.7 KV. 1 ml regeneration buffer was then added into the mixture, and the mixture was placed at 30° C. overnight. 10 ml of top agar at 50° C. containing 30 µg/ml of hygromycin B was added and the mixture was then poured on a top agar containing 30 µg/ml of hygromycin B. After 3-5 days of cultivation at 30° C., the transformants were observed.

G. Screening and Confirmation of the Transformants (1) Few hyphae and spores of the transformant were sampled to place on a slide, added a drop of distilled water, covered with a cover slide and observed under light microscopy. Green fluorescence of hyphae and spore were observed under GFP filter (Ex. 430-510 nm; Em. 475-575 nm).

(2) The transformant was grown in PDB (potato dextrose broth) at 30° C. with 200 rpm vibration for 5-10 days. The culture were homogenized and the chromosomal DNA was extracted. PCR was performed with HPH-EGFP specific primers and a product of 1740 bp was obtained.

H. Confirmation of the Smallest Fragment Having Promoter Activity

To further confirm the smallest fragment of Hsp promoter (1478 bp) having promoter activity, PCR products having 1036 bp, 720 bp, and 497 bp fragments of Hsp promoter were prepared from pMS-Hsp. The primers for the preparation of these PCR products are listed below.

```
497 bp:
Forward primer:
CCGAGAGCGCGTATATGTAACG     (SEQ ID NO: 19)
```

-continued

```
Reverse primer:
CTGATAGAGCAGATAGATAGATG          (SEQ ID NO: 20)

720 bp:
Forward primer:
TGAATTGTGTGGGTGCGTGG             (SEQ ID NO: 21)

Reverse primer:
CTGATAGAGCAGATAGATAGATG          (SEQ ID NO: 20)

1036 bp:
Forward primer:
CAGTGCATCTTAGCGGTTGG             (SEQ ID NO: 22)

Reverse primer:
CTGATAGAGCAGATAGATAGATG          (SEQ ID NO: 20)

1478 bp:
Forward primer:
AGTGGCAGCCAACCCTCACC             (SEQ ID NO: 23)

Reverse primer:
CTGATAGAGCAGATAGATAGATG          (SEQ ID NO: 20)
```

The PCR products having 1478 bp, 1036 bp, 720 bp, and 497 bp fragments of Hsp promoter were cloned into expression vectors and the expression vectors were then transformed into Monascus BCRC 38072 and screened by PDA plate containing Hygr 30 ug/ml. The results are shown as below.

| promoter size | Hyg resistance[1] | Fluorescence[2] |
|---|---|---|
| 1478 bp | R | + |
| 1036 bp | R | N.D. |
| 720 bp | R | N.D. |
| 497 bp | R | + |

[1] R: resistance; N.R.: non-resistance.
[2] +: positive; −: negative.
N.D.: not detected.

The smallest fragment having promoter activity is 497 bp. The fluorescence can be detected in the transformant containing the fragment of 497 bp.

These plasmids were also transformed into Monascus pilosus BCRC 31527 and Neurospora crassa BCRC 32685 and screened by PDA plate containing Hyg$^r$ 50 ug/ml or 200 ug/ml. The results are shown as below.

| Species | Hyg resistance[1] | Fluorescence[2] |
|---|---|---|
| M. sp. BCRC 38072 | R | + |
| M. pilosus | R | + |
| N. crassa | R | − |

[1] R: resistance; N.R.: non-resistance.
[2] +: positive; −: negative.

The smallest fragments of Hsp promoter having promoter activity was confirmed as 497 bp (SEQ ID NO: 24) and can be expressed in Monascus BCRC 38072, Monascus pilosus BCRC31527, and Neurospora crassa BCRC326.

OTHER EMBODIMENTS

The embodiments of the expression vector can be obtained by PCR amplifying and ligating the embodiment of the promoter sequence with a labeling gene in a downstream region thereof. The labeling gene can be, for example, hygromycine resistant gene or hyg-GFP and the expression vector is then constructed as a marker for transformation screening, for example, the estimation of gene cloning efficiency.

The embodiments of the promoter sequence can also be ligated with a labeling gene and a desired target gene at a downstream region thereof for in vivo or in situ detection of protein reaction or active sites in the target protein.

In the embodiments of the expression system, the transformants, and the method for protein expression in the invention, the promoter can be ligated with a desired enzyme gene such as protease, amylase, chitinase, phytase, glucoamylase at a downstream region thereof. Using this system, the production time of these enzymes can be shortened and the production rate can be largely increased. For example, the increased production rate of Monascus protease enhances the efficiency of soybean as a culturing medium, and the cost can be reduced. In addition, the increased production rate of Monascus amylase enhances the saccharification of Monascus during wine-making, resulting in improvement of the process and the development of new wines.

In other embodiments of the expression system, transformants, and methods for protein expression, the promoter can be ligated with genes of secondary metabolites such as polyketide synthase, or nonribosomal peptide synthase gene at a downstream region thereof. This system provides advanced production time of the secondary metabolites thereby increasing the production rate and greatly reducing the cost.

Moreover, transcriptional activator genes can be inserted into the downstream of the embodiment of the promoter in the vector, and genes regulated by the activator can be activated by the over-expressed activator, thereby greatly increasing the production rate.

While the invention has been described by way of example and in terms of preferred embodiment, it is to be understood that the invention is not limited thereto.

What is claimed is:

1. A DNA molecule, comprising a nucleotide sequence of about 517 to about 1116 contiguous nucleotides of SEQ ID NO: 1, wherein the DNA molecule has promoter activity.

2. The DNA molecule as claimed in claim 1, wherein the DNA molecule comprises a nucleotide sequence of about 367 to about 1116 contiguous nucleotides of SEQ ID NO: 1.

3. The DNA molecule as claimed in claim 1, wherein the DNA molecule comprises a nucleotide sequence of about 117 to about 1116 contiguous nucleotides of SEQ ID NO: 1.

4. The DNA molecule as claimed in claim 1, wherein the DNA molecule is obtained from bacteria or fungi.

5. The DNA molecule as claimed in claim 1, wherein the DNA molecule is optained from *Monascus* sp.

6. The DNA molecule as claimed in claim 1, wherein the DNA molecule is obtained from *Monascus pilosus, Monascus ruber*, or *Monascus purpureus*.

7. The DNA molecule as claimed in claim 6, wherein the DNA molecule is obtained from PTA-5687 deposited in the American Type Culture Collection.

8. A recombinant DNA, comprising:
a promoter region comprising a nucleotide sequence of about 517 to about 1116 contiguous nucleotides of SEQ ID NO: 1; and
a coding region comprising a nucleotide sequence encoding a desired protein.

9. The recombinant DNA as claimed in claim 8, wherein the promoter region comprises a nucleotide sequence of about 367 to about 1116 contiguous nucleotides of SEQ ID NO: 1.

10. The recombinant DNA as claimed in claim 8, wherein the promoter region comprises a nucleotide sequence of about 117 to about 1116 contiguous nucleotides of SEQ ID NO: 1.

11. The recombinant DNA as claimed in claim 8, wherein the promoter region is derived from *Monascus* sp.

12. The recombinant DNA as claimed in claim 8, wherein the promoter region is obtained from *Monascus pilosus, Monascus ruber*, or *Monascus purpureus*.

13. The recombinant DNA as claimed in claim 12, wherein the promoter region is obtained from PTA-5687 deposited in the American Type Culture Collection.

14. An expression vector comprising a promoter comprising a nucleotide sequence of about 517 to about 1116 contiguous nucleotides of SEQ ID NO: 1.

15. The expression vector as claimed in claim 14, wherein the promoter comprises a nucleotide sequence of about 367 to about 1116 contiguous nucleotides of SEQ ID NO: 1.

16. The expression vector as claimed in claim 14, wherein the promoter comprises a nucleotide sequence of about 117 to about 1116 contiguous nucleotides of SEQ ID NO: 1.

17. The expression vector as claimed in claim 14, wherein the promoter is obtained from *Monascus* sp.

18. The expression vector as claimed in claim 14, wherein the promoter is obtained from *Monascus pilosus, Monascus ruber*, or *Monascus purpureus*.

19. The expression vector as claimed in claim 18, wherein the promoter is obtained from PTA-5687 deposited in the American Type Culture Collection.

* * * * *

SEQUENCE LISTING

<160> NUMBER OF SEQ ID NOS: 24

<210> SEQ ID NO 1
<211> LENGTH: 1116
<212> TYPE: DNA
<213> ORGANISM: Monascus BCRC 38072

```
<400> SEQUENCE: 1
actattagcg aaagaccggc aagtagatgg aagagccgga attattcttg ttcttcgata        60
gtattccgtc catgcctagg cacagatagt aagatacaca tcgtaatagg accgcctgtc       120
gatgcaatcg ggcaatccag gaacccacgc agcccaaaca cgaggctaga ctcgcgtctg       180
ctgcacatgg aagctgatgg atacatatac ccccagcagc atgcggttcc ccctgcagag       240
accagaggct agaagtctct gggcgcatgt atgtatctat tattacctat caatcggttt       300
cgggtactcc ttgccggagt cgctgaagcg cagacgtgcc gacccggaac atttaggaag       360
aaaccgtgat gattgggatc ggactcgggc acacatggca ccgaattgcc aaaaaatggc       420
gcattctggg gaatcaagca tgcagcacat cttactagat tcaatagatt aaggcacagg       480
ccatgtagag ggcagtggca atacaatatg gggccgtgcg gatccgagga taaaacttgc       540
ccgttagtcc ggctggggt acggcagtc ataaccatct acagccacgg ccgggccagg         600
tggtgcacac ggccgtcccg gtattgtccg aggctcagcc gagaagccct aaccccctagc      660
cgaccagggc tccgcgtctc cccgcaaact cgttttaaac ttgcagcttc ccgtgctccg       720
tcgtgcccta gcccgcgctg attcgccgct cgggcgaatt cgggcgtgtt tatgcctcgt       780
cctgctctga cttcatcgtc cggagcccaa ttcctggccg tcaatcgctc tccttcgctg       840
ccctgacgca aaccgcgctg tccacagcgc tccccatctc gcaacgaccc cgacatctcc       900
cgttatacgg tggagacgga cgagaaatct tctgcggatg ggaggcatat tcgacacttt       960
acgacttatc gtcgccctca tggtttcccc cgctgcaaac attccatata ccccccctcc      1020
ggccctgctt ctcctgctcc tgcaaactcg gattttgttc gacagcaagt cgcgagacag      1080
cagaagaacg actaccactc gacctcactc agaaac                                1116

<210> SEQ ID NO 2
<211> LENGTH: 1478
<212> TYPE: DNA
<213> ORGANISM: Monascus BCRC 38072

<400> SEQUENCE: 2
agtggcagcc aaccctcacc aaatcggaac tgaacagatt tacgttgaag aacgccgtac        60
tcgtaccaat acctacggtg gaaatgccaa cttggagct ggcaggggtg gcgctggccg        120
tggtcgtgct ggacaaggcc ggggcggctt ccaacgagat ggcggccgtg gagggtttgc       180
tccccgtggc cgtggcggaa acgtcacgcc caagggccgc aaccagcctc aaactgcata       240
aagtaaggat gccaatgaga attcgaatgc gtgatgcttt ctttgtttct ccggctgacg       300
atacctcttt ttcttttttt ctaccaatcc cgctggttgg tgcagcgctg atctttgtta       360
tattgcttac ggaatttcca ggttatgtat tactttccca tttacccata atgatatgtg       420
ttatgtggct ctcatttgt cacagtgcat cttagcggtt ggaaaaaagt tttcattttt        480
cccagctcag cactttttatt ttccatggcc tctttggttt gtgttttatg agctcgtttc     540
ttttgttact ttctgccttt gtattgtccg catccgtgtg atcctagcat agcgcgcaga       600
aagcctatat tcttctcccc tattattcca catatccttt tctttctcct tgatgctgtg       660
tttcagatct caacctaaca acacttagtg ttctcttctt tctatttctt attttttattt      720
ttatttattt atattttttc acattggtat tggcaccctg aattgtgtgg gtgcgtggaa       780
tactgtacaa tcaatccact caggcgcagt gaattggttt gcaggaaggg aacagtatat       840
ggatatctgc aaatatgcta gaatacactt ttagctaatg taaaacaatc agtgaattct       900
gaagcttctc agggttgctg cgccaacagg gctggcggag agcaagggcg gagggcggac       960
```

-continued

```
aggcttgtac gatgactggc cccgagagcg cgtatatgta acggtactgt aatgtagtca    1020
cccgcggcag cgatattgca gttaagatac tgtaatgctc tgtaacggca gccggccgaa    1080
caatggaatg ggtggagcgg aacgttctag attgttcaag acctcaggta gcaattgcct    1140
cacccctcca gtttcctcga aggcagacta gaaaaatgca gaaggaaaga gaggcttcca    1200
acggattcga tggctatatc ctgtgattgg aaaaacacga atttccagtg tgtccggatc    1260
cacggaaagc actggaacca agtgaaagtg cagagttcaa agctggttga gcccccaaag    1320
tggtttaggg cacggcggag cgcgtggaag ttgctggacg gccgtagaat cgcagattcc    1380
tgctctcttc cctcgcaact attttatcct cgcttcctcc gcttctctct ctctctttct    1440
tccgcttcat ctattcatct atctatctgc tctatcag                            1478
```

<210> SEQ ID NO 3
<211> LENGTH: 20
<212> TYPE: DNA
<213> ORGANISM: Artificial Sequence
<220> FEATURE:
<223> OTHER INFORMATION: Phosphoenolpyruvate caboxykinase (acuF) forward
      primer designed according to Monascus database

<400> SEQUENCE: 3

```
tgttaatagg accgccctgc                                                   20
```

<210> SEQ ID NO 4
<211> LENGTH: 19
<212> TYPE: DNA
<213> ORGANISM: Artificial Sequence
<220> FEATURE:
<223> OTHER INFORMATION: Phosphoenolpyruvate caboxykinase (acuF) reverse
      primer designed according to Monascus database

<400> SEQUENCE: 4

```
agtatgcggt cagagcacc                                                    19
```

<210> SEQ ID NO 5
<211> LENGTH: 465
<212> TYPE: DNA
<213> ORGANISM: Artificial Sequence
<220> FEATURE:
<223> OTHER INFORMATION: acuF probe
<220> FEATURE:
<221> NAME/KEY: misc_feature
<222> LOCATION: (36)..(36)
<223> OTHER INFORMATION: n is a, c, g, or t

<400> SEQUENCE: 5

```
tgttaatagg accgccctgc accctggtgg tgttcnttac gtcttccttt cctgccttgt      60
tgctgctgct tccgttgcat actacatcta tcgcaccaag acaacaaca ggtcttgctg      120 ttctcttttc ttattgcttt ttctcttttt tctccgttct actctccatc gttccttccc     180
catgactcaa cctcgctaac atctgctttc ttttctgctc tttctaggcc gggcaaagga    240
cacacggagc ttgaggagga gctccatgag acagcgcaca ttgactatga ccagtggca     300 atcgtaagat cccagtcatc ctcttgatgt tttcctcctt gacaaggaca tggctaacga    360
acgactctag attgcgaatc cttccgttgc tgccctctac gaagatgccc ttgtctatga    420
aacgggaacc gccatcacat ccagcggtgc tctgaccgca tactc                     465
```

<210> SEQ ID NO 6
<211> LENGTH: 34
<212> TYPE: DNA
<213> ORGANISM: Artificial Sequence

```
<220> FEATURE:
<223> OTHER INFORMATION: primer bind

<400> SEQUENCE: 6
gaagatctct cgtatgttgt gtggaattgt gagc                                34

<210> SEQ ID NO 7
<211> LENGTH: 30
<212> TYPE: DNA
<213> ORGANISM: Artificial Sequence
<220> FEATURE:
<223> OTHER INFORMATION: primer bind

<400> SEQUENCE: 7
atggtacctg tttctgagtg aggtcgagtg                                     30

<210> SEQ ID NO 8
<211> LENGTH: 20
<212> TYPE: DNA
<213> ORGANISM: Artificial Sequence
<220> FEATURE:
<223> OTHER INFORMATION: mptc3161-A forward primer designed according to
      Monascus database

<400> SEQUENCE: 8
gcttatctcc aatgcctccg                                                20

<210> SEQ ID NO 9
<211> LENGTH: 18
<212> TYPE: DNA
<213> ORGANISM: Artificial Sequence
<220> FEATURE:
<223> OTHER INFORMATION: mptc3161-B reverse primer designed according to
      Monascus database

<400> SEQUENCE: 9
caaggtctcg ctcgttac                                                  18

<210> SEQ ID NO 10
<211> LENGTH: 264
<212> TYPE: DNA
<213> ORGANISM: Artificial Sequence
<220> FEATURE:
<223> OTHER INFORMATION: Hsp probe

<400> SEQUENCE: 10
gcttatctcc aatgcctccg atgccctcga caagatccgc tatgagtcct tgtcggaccc    60
ttccaagctc gattcgtgca aggacctccg tatcgacatc atcccggata aggagtctaa   120
gactctcacc atccgcgata ccggtattgg tatgaccaag gctgatctaa tcaacaacct   180
tggtaccatt gctcgctctg aacataacc atactggttc cgactagatt agttgttgga   240
accatggtaa cgagcgagac cttg                                          264

<210> SEQ ID NO 11
<211> LENGTH: 20
<212> TYPE: DNA
<213> ORGANISM: Artificial Sequence
<220> FEATURE:
<223> OTHER INFORMATION: Mps17-9259-F forward primer designed from
      Monascus database

<400> SEQUENCE: 11
agtggcagcc aaccctcacc                                                20
```

-continued

<210> SEQ ID NO 12
<211> LENGTH: 27
<212> TYPE: DNA
<213> ORGANISM: Artificial Sequence
<220> FEATURE:
<223> OTHER INFORMATION: Mps-17-7782-R reverse primer designed from
      Monascus database

<400> SEQUENCE: 12
cgggctgata gagcagatag atagatg                                        27

<210> SEQ ID NO 13
<211> LENGTH: 30
<212> TYPE: DNA
<213> ORGANISM: Artificial Sequence
<220> FEATURE:
<223> OTHER INFORMATION: acuF-B2 forward primer

<400> SEQUENCE: 13
gaagatcttg tcgatgcaat cgggcaatcc                                     30

<210> SEQ ID NO 14
<211> LENGTH: 30
<212> TYPE: DNA
<213> ORGANISM: Artificial Sequence
<220> FEATURE:
<223> OTHER INFORMATION: acuF-KpnI reverse primer

<400> SEQUENCE: 14
atggtacctg tttctgagtg aggtcgagtg                                     30

<210> SEQ ID NO 15
<211> LENGTH: 30
<212> TYPE: DNA
<213> ORGANISM: Artificial Sequence
<220> FEATURE:
<223> OTHER INFORMATION: acuF-B3 forward primer

<400> SEQUENCE: 15
gaagatcttg atgattggga tcggactcgg                                     30

<210> SEQ ID NO 16
<211> LENGTH: 28
<212> TYPE: DNA
<213> ORGANISM: Artificial Sequence
<220> FEATURE:
<223> OTHER INFORMATION: acuF-B4 forward primer

<400> SEQUENCE: 16
gaagatcttg cggatccgag gataaaac                                       28

<210> SEQ ID NO 17
<211> LENGTH: 28
<212> TYPE: DNA
<213> ORGANISM: Artificial Sequence
<220> FEATURE:
<223> OTHER INFORMATION: acuF-B5 forward primer

<400> SEQUENCE: 17
gaagatctcc cggtattgtc cgaggctc                                       28

<210> SEQ ID NO 18
<211> LENGTH: 600
<212> TYPE: DNA
<213> ORGANISM: Monascus BCRC 38072

-continued

<400> SEQUENCE: 18

```
tgcggatccg aggataaaac ttgcccgtta gtccggctgg gggttacggc agtcataacc      60
atctacagcc acggccgggc caggtggtgc acacggccgt cccggtattg tccgaggctc     120
agccgagaag ccctaacccc tagccgacca gggctccgcg tctccccgca aactcgtttt     180
aaacttgcag cttcccgtgc tccgtcgtgc cctagcccgc gctgattcgc cgctcgggcg     240
aattcgggcg tgtttatgcc tcgtcctgct ctgacttcat cgtccggagc ccaattcctg     300
gccgtcaatc gctctccttc gctgccctga cgcaaaccgc gctgtccaca gcgctcccca     360
tctcgcaacg accccgacat ctcccgttat acggtggaga cggacgagaa atcttctgcg     420
gatgggaggc atattcgaca ctttacgact tatcgtcgcc ctcatggttt ccccgctgc      480
aaacattcca tataccccc cttcggccct gcttctcctg ctcctgcaaa ctcggattt       540
gttcgacagc aagtcgcgag acagcagaag aacgactacc actcgacctc actcagaaac    600
```

<210> SEQ ID NO 19
<211> LENGTH: 22
<212> TYPE: DNA
<213> ORGANISM: Artificial Sequence
<220> FEATURE:
<223> OTHER INFORMATION: primer bind

<400> SEQUENCE: 19

```
ccgagagcgc gtatatgtaa cg                                              22
```

<210> SEQ ID NO 20
<211> LENGTH: 23
<212> TYPE: DNA
<213> ORGANISM: Artificial Sequence
<220> FEATURE:
<223> OTHER INFORMATION: primer bind

<400> SEQUENCE: 20

```
ctgatagagc agatagatag atg                                             23
```

<210> SEQ ID NO 21
<211> LENGTH: 20
<212> TYPE: DNA
<213> ORGANISM: Artificial Sequence
<220> FEATURE:
<223> OTHER INFORMATION: primer bind

<400> SEQUENCE: 21

```
tgaattgtgt gggtgcgtgg                                                 20
```

<210> SEQ ID NO 22
<211> LENGTH: 20
<212> TYPE: DNA
<213> ORGANISM: Artificial Sequence
<220> FEATURE:
<223> OTHER INFORMATION: primer bind

<400> SEQUENCE: 22

```
cagtgcatct tagcggttgg                                                 20
```

<210> SEQ ID NO 23
<211> LENGTH: 20
<212> TYPE: DNA
<213> ORGANISM: Artificial Sequence
<220> FEATURE:
<223> OTHER INFORMATION: primer bind -continued

```
<400> SEQUENCE: 23
agtggcagcc aaccctcacc                                                  20

<210> SEQ ID NO 24
<211> LENGTH: 497
<212> TYPE: DNA
<213> ORGANISM: Monascus BCRC 38072

<400> SEQUENCE: 24
ccgagagcgc gtatatgtaa cggtactgta atgtagtcac ccgcggcagc gatattgcag       60
ttaagatact gtaatgctct gtaacggcag ccggccgaac aatggaatgg gtggagcgga      120
acgttctaga ttgttcaaga cctcaggtag caattgcctc accoctccag tttcctcgaa      180 ggcagactag aaaaatgcag aaggaaagag aggcttccaa cggattcgat ggctatatcc      240
tgtgattgga aaaacacgaa tttccagtgt gtccggatcc acggaaagca ctggaaccaa      300
gtgaaagtgc agagttcaaa gctggttgag cccccaaagt ggtttagggc acggcggagc      360
gcgtggaagt tgctggacgg ccgtagaatc gcagattcct gctctcttcc ctcgcaacta      420 tttatcctc gcttcctccg cttctctctc tctctttctt ccgcttcatc tattcatcta      480
tctatctgct ctatcag                                                    497
```